United States Patent [19]

Bennett

[11] Patent Number: Plant 5,424

[45] Date of Patent: Apr. 2, 1985

[54] MINIATURE ROSE PLANT

[76] Inventor: Cecilia L. D. Bennett, 489 Minot Ave., Chula Vista, Calif. 92010

[21] Appl. No.: 525,454

[22] Filed: Aug. 22, 1983

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant, named 'POPS', which is characterized by its abundance of deep pink blooms of exhibition-quality.

1 Drawing Figure

1

The present invention relates to a new and distinct variety of a hardy, dwarf, bush plant of the miniature class; the variety being primarily characterized as a deep pink.

The variety is further characterized by:

Long stemmed blooms, borne singly or in sprays of 3 to 5 or more, held very erect and well above the foliage.

Has a slight fragrance.

The plant ranges in height from 12 to 18 inches. The canes are sturdy and erect, heavily branched with medium to heavy foliage covering. The plant is a prolific bloomer that does well either outdoors or in the green house.

The plant has good growth habits, well shaped and attractive in appearance, bearing numerous leaflets of average size.

The seed parent was Sheri Anne (U.S. Plant Pat. No. 3,826), and the pollen parent was Little Girl (Miniature Rose Plant, pink blend; R. S. Moore; introduced by Sequoia Nursery, 1973).

Subsequent to the origination of the variety, I have successfully reproduced it at Tiny Petals Nursery located at aforesaid retaining the distinguishing characteristics through succeeding propagations by cuttings.

The descriptive matter which follows pertains to roses grown and color values observed in plants and newly opened blooms in the months of July and August. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant named 'POPS', the following is a detailed description thereof in outline; all major color plate identifications being by reference to The British Colour Council Horticultural Colour Chart, except where common terms of color definition are employed.

Type: Hardy, dwarf, bushy, green house or outdoor, exhibition quality of garden decorative potted plant.

Class: Miniature.

Variety name: POPS.

Flowers borne: Usually one to a stem, but occasionally in sprays of 3 to 5 or more on erect stems with foliage well below the blooms.

Quantity of blooms: Heavy both outdoors or green house grown.

Bud:

2

*Peduncle.*—Average length (20 to 30 mm); average diameter and sturdy; near Pod Green (061 page 120) with light to occasionally heavy tinting of bronze.

*Hairs.*—Extremely small and numerous; located over entire surface of peduncle, calyx tube and sepals.

*Calyx.*—Color is near Pod Green (061 page 120).

*Opening.*—Opens well in all weather.

Bloom:

*Size when fully open.*—Average for a miniature variety (35 to 40 mm).

*Petalage.*—Double — Averaging about 15 to 20 petals, arranged regularly, plus petaloids (8 to 12 or more).

*Form.*—Urn-shaped to ovoid as the bloom progresses. The petals remain at first somewhat tightly cupped with the tips and/or margins reflexed outward, becoming at maturity more loosely cupped, with the margins rolling under loosely, forming a soft peak at the apex of each petal. This is most noticeable on the outermost row of petals.

Petals: Fairly thick with good substance; matte finish.

*Shape.*—Outer petals are of a broad obovate form with a slight peak at the apex. The intermediate petals are very much like the outer petals only slightly narrower. The inner petals are narrower yet; some may even be called broad lanceolate in form. The petaloids are like small lanceolates with occasional irregularities in shape.

Color (newly opened flowers from plants grown outdoors (July and August 1983), Chula Vista, Calif.):

*Outside petals.*—Upper surface — Ranging from near Carmine Rose (621 to 621/1 page 21) to near Porcelain Rose (620 to 620/1 page 147) on the upper third to half of the petal. Ranging from near Carmine Rose (621/1 to 621/2 page 21) to near Porcelain Rose (620/1 to 620/2 page 147) on the rest of the petal, except for a small area at the base of white with a tip of Naples Yellow (403 to 403/1 page 121).

*Under surface.*—Ranging from near Carmine Rose (621/2 to 621/3 page 21) to near Porcelain Rose (620/2 to 620/3 page 147), except for a small area at the base of white with a tip of Naple Yellow (403/1 to 403/2 Page 121).

*Intermediate petals.*—Same as outside petals.

*Inner petals.*—Upper surface — Ranging from near Carmine Rose (621 to 621/1 page 21) to near Porcelain Rose (620 to 620/1 page 147), except for a tip of Naples Yellow (430 page 121). Under Surface — Ranging from near Carmine Rose (621/1 to 621/2 page 21) to near Procelain Rose (620/1 to 620/2 page 147), except for a small area at the base of white with a tip of Naples Yellow (403to 403/1 page 121).

*Flower longevity.*—(August 1983) Plant in pot 3 to 5 days from bud with sepals down to fully opened bloom. Holding at fully open with only slight fading of color for an additional 3 to 4 days before bloom begin to drop petals. Cut blooms at living-room temperature 3 to 5 days or longer from bud to fully open bloom.

Reproductive organs:

*Stamens.*—Generous amount arranged uniformly around the pistil.

*Filaments.*—Varying in length; pale yellow in color.

*Pollen.*—Abundant.

*Pistil.*—Long, abundant and compact; pale green in color.

*Styles.*—Long; pale green in color.

*Ovaries.*—All encased in calyx.

*Hips.*—Some.

*Seed.*—Few or none.

*Sepals.*—Permanent; spear-shaped; open as the bloom opens, but does not recurve against the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze, especially noticeable on the newer foliage.

*Color.*—Ranging from near Lettuce Green (861 through 861/3 page 176) to near Spinach Green (0960 through 0960/2 page 187), some bronzing of the margins and newer leaves. The upper surfaces have a satiny finish, and the under surfaces have a matte finish of a slightly lighter shade than the upper surfaces.

*Rachis.*—Medium strength; upper surface is grooved with very small hairs over the length of it. Under surface also contains many very small hairs and some small hooked thorns as well.

*Stipules.*—Varying in length from short to medium; average width; tapering auricles angled outward at about 45 degrees.

Growth:

*Habit.*—Dwarf, bushy, much branched; average height for a miniature rose plant.

*Growth.*—Moderate.

*Canes.*—Medium; sturdy; held very erect.

*Main stems.*—Color — Ranging from near Lettuce Green (861 through 861/2 page 176) to near Scheeles Green (860 through 860/2 page 175) with little or no bronzing.

*Thorns.*—Averaging 12 to 20 per 10 cm on the main stems and branches. Pale yellow to reddish in color with occasional bronzing; average size for a miniature rose plant; slender; may be straight (most typical on the main stems and branches) or slightly hooked downward (most typical on the underside on the rachis).

*Branches.*—Color — Same as main stems.

The miniature rose plant and its flowers as herein described may vary in slight detail due to climatic, soil and cultural conditions under which the variety may be grown; the present description being of the variety as grown at Chula Vista, Calif.

The following is claimed:

1. A new and distinct variety of miniature rose plant named 'POPS' of hardy, dwarf, bushy, much branched habit, substantially as illustrated and described, characterized by its abundance of deep pink blooms of exhibition quality, usually borne singly or in sprays of 3 to 5 or more, which may be propagated from cuttings, and grows well outdoors or in the green house.

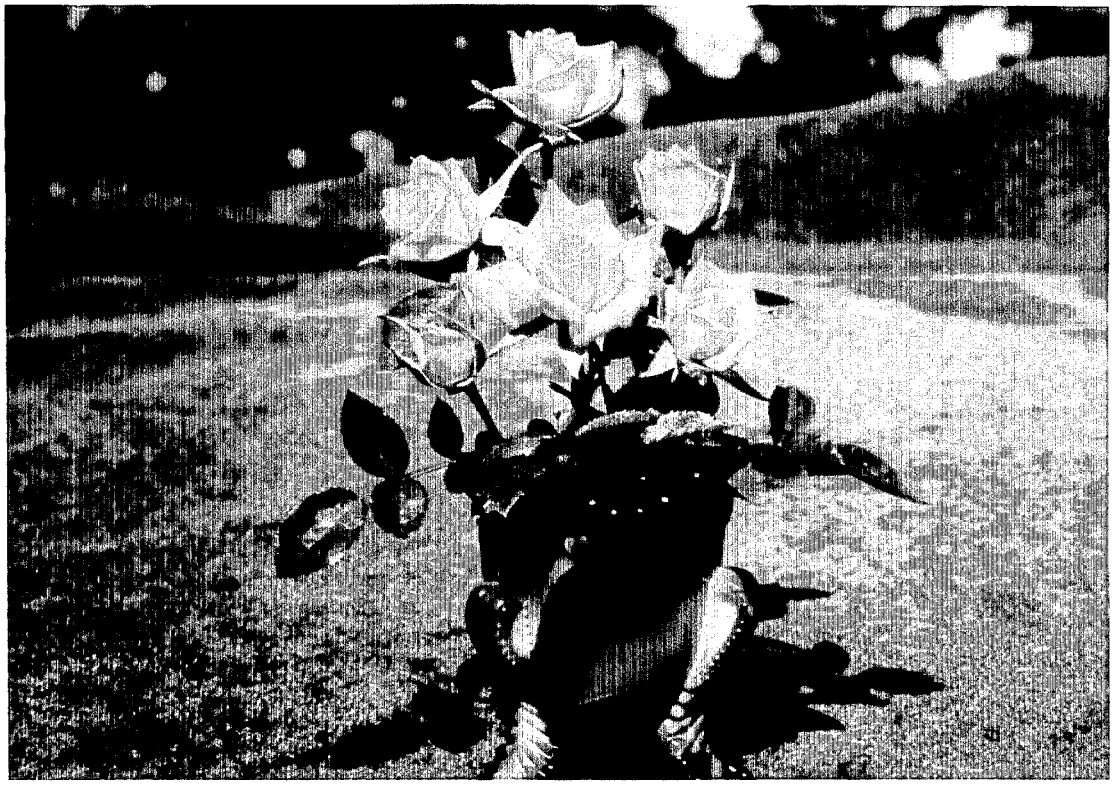

* * * * *